United States Patent [19]

White, Jr.

[11] 4,049,650

[45] Sept. 20, 1977

[54] 1-[[[5-(SUBSTITUTED PHENYL)-2-OXAZOLYL]METHYLENE]-AMINO]-2,4-IMIDAZOLIDINEDIONES

[75] Inventor: Ralph L. White, Jr., Norwich, N.Y.

[73] Assignee: Morton-Norwich Products, Inc., Norwich, N.Y.

[21] Appl. No.: 733,296

[22] Filed: Oct. 18, 1976

[51] Int. Cl.$^2$ ............................................. C07D 405/06
[52] U.S. Cl. ...................................... 542/400; 548/300
[58] Field of Search ............ 260/240 G, 307 R, 309.5; 423/273

[56] References Cited

U.S. PATENT DOCUMENTS

| | | | |
|---|---|---|---|
| 3,415,821 | 12/1968 | Davis et al. | 260/240 G |
| 3,803,136 | 4/1974 | Schwan et al. | 260/240 G |
| 3,843,636 | 10/1974 | White, Jr. | 260/240 G |

Primary Examiner—Allen B. Curtis
Attorney, Agent, or Firm—Anthony J. Franze

[57] ABSTRACT

A series of 1-[[[5-(substituted phenyl-2-oxazolyl]methylene]amino]-2,4-imidazolidinediones are useful as muscle relaxants.

11 Claims, No Drawings

1-[[[5-(SUBSTITUTED PHENYL)-2-OXAZOLYL]METHYLENE]AMINO]-2,4-IMIDAZOLIDINEDIONES

This invention relates to chemical compounds. More particularly it is concerned with a series of compounds of the formula:

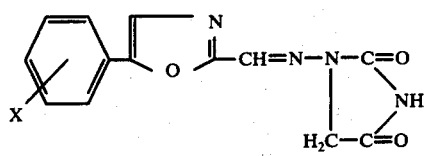

wherein X represents hydrogen, 4-halo, 3,4-dichloro, 4-nitro, 4-methoxy, 4-methyl or 3-trifluoromethyl.

The members of this series of compounds possess pharmacological activity. They are particularly noteworthy for the skeletal muscle relaxant effect elicited by them when administered to warm blooded animals. Upon intravenous administration to rats using a dose of about 36 mg/kg inhibition of the gastrocnemius muscle twitch is secured. Suitable vehicles for intraveneous administration include those pharmaceutically acceptable menstrua such as dimethylsulfoxide, dimethylacetamide and aqueous mannitol-sodium hydroxide mixture.

The members of this series of compounds are readily formulated into pharmaceutical compositions such as tablets, elixirs, solutions, suspensions, capsules and the like using adjuvants and excipients commonly employed for such purposes and with which there is no incompatibility. Where dictated by reason of greater aqueous solubility the members of this series are readily converted into salt form such as the sodium salt by reaction with a basic reagent such as sodium hydroxide.

The method for preparing the members of this series which is currently preferred is briefly described by the following schema:

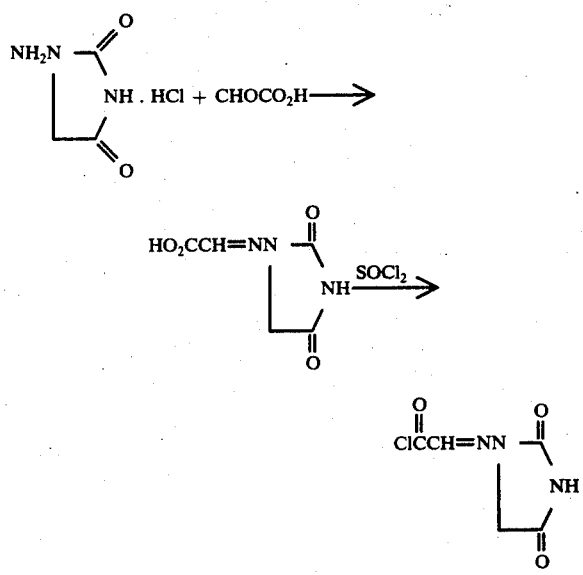

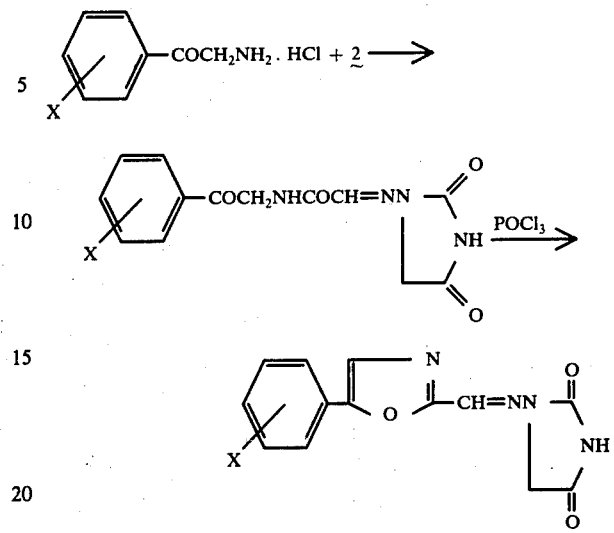

wherein X has the significance given above. In this schema the [(2,4-dioxo-1-imidazolidinyl)iminomethyl]-formic acid was prepared as follows: Glyoxalic acid (37.0 g, 0.50 mole) was dissolved in 100 ml of water and the solution was filtered into an erlenmeyer flask. 1-Aminohydantoin hydrochloride (75.5 g, 0.50 mole) was dissolved in 400 ml of water and the solution was filtered into the same erlenmeyer flask. The two solutions were swirled together and a white precipitate formed immediately. The mixture stood for 0.5 hour and the white solid was filtered off. A yield of 62 g (73%) was obtained, m.p. 258°–260°.

Anal. Calcd. for $C_5H_5N_3O_4$: C, 35.04; H, 2.96; N, 24.56; Found: C, 34.96; H, 2.96; N, 24.77.

Its acid chloride was prepared in this fashion:

The acid (171 g, 0.20 ml) was combined with dioxane (1500 ml) and thionyl chloride (250 ml). The stirred mixture was allowed to reflux for three hr before dissolution occurred and was refluxed for two additional hr. The solvent was removed by distillation under reduced pressure and the remaining solid was recrystallized from nitromethane (1500 ml). A yield of 113.7 g (60% yield) was isolated, m.p. 197°–207°.

In order that this invention may be readily understood by and available to those skilled in the art the following examples are supplied.

EXAMPLE I

1-[[[5-(3,4-Dichlorophenyl)-2-oxazolyl]methylene]-amino]-2,4-imidazolidinedione

A. 2-Amino-3',4'-dichloroacetophenone Hydrochloride

3',4'-Dichloroacetophenene (100 g, 0.530 mole) was combined with a solution of glacial acetic acid (200 ml) and 48% HBr (2.0 ml). To the stirred mixture was added a solution of bromine (86 g, 30.4 ml, 0.53 mole) and glacial acetic acid (100 ml) dropwise over a period of 1.5 hr. The mixture continued to stir for 0.5 hr then was poured into water (2000 ml). The resulting yellow solid was collected, washed with additional water, and allowed to air dry. The product was recrystallized from ethanol (200 ml) and 89 g was collected (63% yield), m.p. 53°–57°.

The above solid (88.8 g, 0.33 mole) was dissolved in chloroform (150 ml) and stirred together with a solution of hexamethylenetetramine (52. g, 0.37 mole) in chloroform (600 ml). The solution was stirred overnight. There were 132 g of the solid collected (95% yield). The solid was combined with methanol (180 ml) and conc. hydrochloric acid (240 ml). The mixture was stirred and refluxed overnight and then was allowed to cool. The solid was collected by filtration and recrystallized (Darco) from methanol (1200 ml). A yield of 60 g of product (90% yield, 56.6% total yield) was obtained, m.p. > 340°.

B. N-(3,4-Dichlorophenacyl)-[[(2,4-dioxo-1-imidazolidinyl)-imino]methyl]formamide To a stirred mixture of the [(2,4-dioxo-1-imidazolidinyl)iminomethyl]formyl chloride (9.5 g, 0.05 mole) and pyridine (100 ml) was added 2-amino-3',4'-dichloroacetophenone hydrochloride (12.0 g, 0.05 mole). The mixture was stirred overnight at room temperature.

The mixture was added to one liter of water and was stirred to yield solid which was collected by filtration and was washed with ethanol and ether. The filtration gave 14.2 g of crude product which was recrystallized (Darco) from dimethylformamide (40 ml) to give 6.7 g of product (38% yield, 21% total yield), m.p. 290°–293.5°.

Anal. Calcd. for $C_{13}H_{10}Cl_2N_4O_4$: C, 43.72; H, 2.82; N, 15.69; Found: C, 43.65; H, 2.72; N, 15.96.

C. A mixture of B (27 g, 0.075 mole) and phosphorus oxychloride (380 ml) was stirred and refluxed overnight. Half of the phosphorus oxychloride was distilled off and the remaining mixture was poured into a stirred mixture of ice and water (4 liters). The product was collected by filtration and washed with ethanol and ether.

The product was allowed to air-dry and was recrystallized from acetic acid (400 ml) to give 11 g (45%). A gram was recrystallized again for analytical purity, m.p. 292°–294°.

Anal. Calcd. for $C_{13}H_8Cl_2N_4O_3$: C, 46.04; H, 2.38; N, 16.52; Found: C, 46.13; H, 2.21; N, 16.64.

EXAMPLE II

1-[[(5-Phenyl-2-oxazolyl)methylene]amino]-2,4-imidazolidinedione

A. N-[2-Phenyl-2-oxoethyl]-[[(2,4-dioxo-1-imidazolidinyl)-imino] methyl]formamide To a stirred mixture of α-aminoacetophenone hydrochloride (50 g, 0.29 mole) and [[(2,4-dioxo-1-imidazolidinyl)imino]methyl]formyl chloride (55 g, 0.29 mole) was added a solution of 600 ml of dimethylformamide and 60 ml of pyridine. The mixture went into solution after 2 hours and the solution was stirred overnight.

The solution was poured into water (3 liters) and a light yellow solid precipitated out of solution. The solid was collected by filtration and washed with ethanol and ether.

The product was dried in the 60° oven and recrystallized from acetic acid (500 ml) to give 46 g (55%) of light yellow product, m.p. 248°–253°.

Anal. Calcd. for $C_{13}H_{12}N_4O_4$: C, 54.16; H, 4.20; N, 19.44; Found: C, 53.91; H, 4.18; N, 19.33.

B. A mixture of A (30 g, 0.10 mole) and phosphorus oxychloride (520 ml) was stirred and refluxed for 0.5 hr. An additional 180 ml of phosphorus oxychloride was added to the very thick mixture. The mixture was stirred and refluxed for another 15 minutes. The solid was collected and added to a mixture of ice and water (4 liters).

The solid was collected and recrystallized from acetic acid (800 ml). The product (23 g) was collected in two crops (78%), m.p. 279°–282°.

Anal. Calcd. for $C_{13}H_{10}N_4O_3$: C, 57.77; H, 3.73; N, 20.74; Found: C, 57.51; H, 3.69; N, 20.76.

EXAMPLE III

1-[[[5(4-Nitrophenyl)-2-oxazolyl]methylene]amino]-2,4-imidazolidinedione

A. N[2-(4-Nitrophenyl)-2-oxoethyl]-[[(2,4-dioxo-1-imidazolidinyl)imino]-methyl]formamide α-Bromo-4-nitroacetophenone (149 g, 0.61 mole) in chloroform (630 ml) is added to hexamethylenetetramine (94 g, 0.67 mole) in chloroform (1260 ml). The mixture is stirred overnight and filtered to yield 203 g of adduct. The adduct is then dissolved in ethanol (1005 ml) and conc. hydrochloric acid (210 ml) and is stirred overnight. The mixture is then filtered and the collected solid is washed with cold ethanol and oven-dried at 60° to yield 205 g (°100%) of α-amino-4-nitroacetophenone hydrochloride, m.p. > 400° (softens at 240°).

In a 1-1 flask are placed the above amine hydrochloride (44 g, 0.20 mole) and [[(2,4-dioxo-1-imidazolidinyl)]methyl]formyl chloride (38 g, 0.20 mole). To the stirred solids is added a solution of pyridine (40 ml) and dimethylformamide (400 ml) and stirring is continued for 18 hrs. The mixture is poured into water (2.0 l) and the insoluble solid is collected. Recrystallization from dimethylformamide gives 44 g (67%), m.p. 275°–279°, in two crops.

Anal. Calcd. for $C_{13}H_{11}N_5O_6$: C, 46.85; H, 3.33; N, 21.02; Found: C, 46.76; H, 3.32; N, 21.27.

B. A mixture of A (24 g, 0.073 mole) and phosphorus oxychloride (730 ml) was stirred and refluxed for two hours. The dark mixture was filtered. The filtrate was concentrated to 150 ml and poured over a stirred ice-water mixture (2 liters). A dark brown solid precipitated out of solution and was collected by filtration. The product was recrystallized from dimethylformamide (100 ml) to yield 9.6 gm (42%), m.p. 314°–316°.

Anal. Calcd. for $C_{13}H_9N_5O_5$: C, 49.53; H, 2.88; N, 22.22; Found: C, 49.41; H, 2.80; N, 22.25.

EXAMPLE IV

1-[[[5-(4-Methoxyphenyl)-2-oxazolyl]methylene]-amino]-2,4-imidazolidinedione

A. N-[2-(4-Methoxyphenyl)-2-oxoethyl]-[[(2,4-dioxo-1-imidazolidinyl)imino]methyl]formamide α-Bromo-4-methoxyacetophenone (50 g, 0.22 mole) was dissolved in 200 ml of chloroform and added to a stirred solution of hexamethylenetetramine (32 g, 0.23 mole) in 400 ml of chloroform. A light colored solid precipitated out of the dark solution and was filtered off after several hours of stirring to yield 80 g of adduct (99%), m.p. 169°–173°.

All of the adduct was combined with ethanol (650 ml) and conc. hydrochloric acid (80 ml). The stirred mixture was refluxed for 2.5 hours and the solid was collected. The product was recrystallized from methanol and 1% conc. hydrochloric acid (500 ml). Product (34 g, 77%) was collected in three crops, m.p. 189°–196°.

All of the above amine hydrochloride (34 g, 0.17 mole) was combined with [[(2,4-dioxo-1-imidazolinyl)imino]methyl]formyl chloride (32 g, 0.17 mole). To the stirred mixture was added a solution of pyridine (45 ml)

and dimethylformamide (450 ml) and stirring of the mixture was continued for 48 hours. The mixture was poured into water (2 liters) and the insoluble solid was collected. Recrystallization from acetic acid (3 liters) yielded 30 g (42%, in two crops), m.p. 285°–287°.

Anal. Calcd. for $C_{14}H_{14}N_4O_5$: C, 52.83; H, 4.43; N, 17.60; Found: C, 52.71; H, 4.39; N, 17.56.

B. The compound of A (18 g, 0.058 mole) was combined with phosphorus oxychloride (300 ml) and the mixture was stirred and refluxed for 5 hr. Phosphorus pentachloride (12 g, 0.060 mole) was added to the stirred mixture and the mixture was allowed to stir for five days.

Another portion of phosphorus pentachloride (12 g, 0.060 mole) was added to the mixture and was stirred and refluxed for 1.5 hours. The mixture was filtered and the filtrate was discarded. The solid was stirred into an ice and water mixture (500 ml) and was collected. The solid was recrystallized from nitromethane (250 ml) and dimethylformamide (200 ml) to give 4.9 g (28%) of product, m.p. 291°–294°.

Anal. Calcd. for $C_{14}H_{12}N_4O_4$: C, 56.00; H, 4.03; N, 18.66; Found: C, 55.68; H, 4.08; N, 18.71.

EXAMPLE V

1-[[[5-(4-Bromophenyl)-2-oxazolyl]methylene]amino]-2,4-imidazolidinedione

A. N-[2-(4-Bromophenyl)-2-oxoethyl]-[[(2,4-dioxo-1-imidazolidinyl)-imino]methyl]formamide To a stirred solution of 2-bromo-4'-bromoacetophenone (100 g, 0.36 mole) in chloroform (500 ml) was added hexamethylenetetramine (50 g, 0.36 mole). The mixture was stirred for 2.5 hr. and 143 g of the addition product was collected by filtration (100%).

The addition product was combined with a solution of methanol (300 ml) and conc. HCl (410 ml), and the mixture was stirred for 52 hours. The solid was collected by filtration and was washed with isopropanol. The product was recrystallized from methanol (Darco) to give 55 g (61%, in three crops), m.p. 284°–287°.

To a stirred mixture of the above amine hydrochloride (55 g, 0.22 mole) and [[(2,4-dioxo-1-imidazolidinyl)imino]methyl]formyl chloride (42 g, 0.22 mole) was added a solution of 440 ml of dimethylformamide and 44 ml of pyridine. The mixture was stirred for 20 hr and poured into two liters of water. The solid was collected by filtration and washed with ethanol and ether. Recrystallization from acetic acid (2200 ml) gave 36 g (28%, 2 crops), m.p. 267°–269°.

Anal. Calcd. for $C_{13}H_{11}BrN_4O_4$: C, 42.52; H, 3.02; N, 15.26; Found: C, 42.61; H, 3.15; N, 15.35.

B. The compound of A (22 g, 0.061 mole) was combined with phosphorus oxychloride (310 ml) and the mixture was stirred and refluxed for seven hours. The solid was filtered off and stirred into an ice and water mixture (1 liter). The product was collected by filtration.

Recrystallization from acetic acid (700 ml) gave 15 g (70%) of product, m.p. 290°–292°.

Anal. Calcd. for $C_{13}H_9BrN_4O_3$: C, 44.72; H, 2.60; N, 16.05; Found: C, 44.81; H, 2.72; N, 15.90.

EXAMPLE VI

1-[[[5-(4-Fluorophenyl)-2-oxazolyl]methylene]amino]-2,4-imidazolidinedione

A. N-[2-(4-Fluorophenyl)-2-oxoethyl)-[[(2,4-dioxo-1-imidazolidinyl)-imino]methyl]formamide 4'-Fluoroacetophenone (122 ml, 138 g, 1.00 mole) was combined with diethyl ether (300 ml) and the solution was cooled to 5°. Bromine (54.5 ml, 1.00 mole) was added dropwise to the stirred solution, keeping the temperature at 5°, over a three hour interval. The solution was washed with water and a dilute solution of sodium carbonate. The ether layer was dried over sodium sulfate and the ether was evaporated under pressure. The remaining solid was dissolved in chloroform (200 ml) and combined with a solution of hexamethylenetetramine (140 g, 1.00 mole) in chloroform (1 liter). A precipitate formed upon addition and stirring was continued for three hours. The addition product was collected and was washed with carbon tetrachloride to give 338 g (95%).

All of the addition product was combined with ethanol (720 ml) and concentrated hydrochloric acid (620 ml). The solution was stirred for 0.5 hour when a light yellow precipitate formed and stirring was continued for 20 hours. The solid was collected and the filtrate was evaporated under reduced pressure. The residue was combined with the collected solid, and the mixture was recrystallized from a solution of methanol (1300 ml) and conc. hydrochloric acid (1%) to give 69.6 g of 2-amino-4'-fluoroacetophenone hydrochloride.

All of the above acetophenone (70 g, 0.37 mole) was combined with [[(2,4-dioxo-1-imidazolidinyl)imino]methyl]formyl chloride (70 g, 0.37 mole). To the stirred mixture was added a solution of 750 ml of dimethylformamide with 75 ml of pyridine and stirring was continued for 50 hours.

The dark orange solution was poured into water (4 liters) and the precipitated solid was collected. Recrystallization from acetic acid gave 65 g (22%), m.p. 281°–282°.

Anal. Calcd. for $C_{13}H_{11}FN_4O_4$: C, 51.15; H, 3.30; N, 18.36; Found: C, 50.96; H, 3.60; N, 18.32.

B. The compound of A (54 g, 0.18 mole) was combined with phosphorus oxychloride (900 ml) and the mixture was stirred and refluxed for 24 hours. The mixture was cooled to room temperature and filtered, and the solid was stirred in a water and ice mixture (2 liters) and collected. Recrystallization from acetic acid gave 28 g (54%), m.p. 281°–282°.

Anal. Calcd. for $C_{13}H_9FN_4O_3$: C, 54.17; H, 3.15; N, 19.44; Found: C, 54.21; H, 3.26; N, 19.26.

EXAMPLE VII

1-[[[5-(4-Methylphenyl)-2-oxazolyl]methylene]amino]-2,4-imidazolidinedione

A mixture of 2-bromo-4'-methylacetophenone (87 g, 0.41 mole), hexamethylenetetramine (63 g, 0.45 mole) and carbon tetrachloride (500 ml) was stirred for 4 hours at room temperature. The adduct product was collected by filtration, washed with ether, and was allowed to air-dry.

To the adduct product was added a solution of ethanol (140 ml) and concentrated hydrochloric acid (84 ml) and the mixture was stirred overnight at room temperature. The mixture was filtered and the solid (ammonium chloride) was discarded. The filtrate was twice extracted with ether and more ammonium chloride was collected. The aqueous layer was allowed to evaporate to dryness and the remaining solid was triturated with isopropanol (300 ml). Recrystallization from isopropanol with 1% HCl (conc.) gave 10.0 g (2 crops, 13%).

To a stirred mixture of the above amine hydrochloride (13 g, 0.068 mole) and [[(2,4-dioxo-1-imidazolidinyl)imino]methyl]formyl chloride (13 g, 0.068 mole) was added a solution of dimethylformamide (140 ml) and pyridine (14 ml). The solution was then stirred for 20 hours at room temperature and was poured into two liters of water. The product precipitated out of solution and was collected by filtration to give 14 g.

Anal. Calcd. for $C_{13}H_{14}N_4O_4$: C, 55.62; H, 4.67; N, 18.54; Found: C, 55.28; H, 4.69; N, 18.75.

A mixture of the above solid (14 g, 0.045 mole) and phosphorus oxychloride (50 ml) was stirred and refluxed for five hours. The mixture was allowed to cool to room temperature. The solid was collected by filtration and stirred into an ice and water mixture (2 liters). The product was collected and recrystallization from acetic acid (200 ml) gave 8.2 g (5.5%; m.p. 272°–276°.

Anal. Calcd. for $C_{14}H_{12}N_4O_3$: C, 59.15; H, 4.25; N, 19.71; Found: C, 59.25; H, 4.41; N, 20.11.

EXAMPLE VIII

1-[[[5-4-Chlorophenyl)-2-oxazolyl]methylene]amino]-2,4-imidazolidinedione

To a stirred, cooled solution of 4-chloroacetophenone (100 g, 0.65 mole), anhydrous ether (650 ml) and dioxane (325 ml) was added bromine (35 ml, 0.65 mole) dropwise over a period of 1.25 hours, keeping the temperature at 20° C (±5° C). The solution was then washed with water (3 × 1 l). The collected ether layer was dried over magnesium sulfate and the ether solution was evaporated under reduced pressure to give a solid. The solid was washed with water, collected by filtration, and air-dried to give the α-bromo-4-chloroacetophenone.

To a stirred solution of hexamethylenetetramine (168 g, 1.2 mole) in chloroform (1525 ml) was added α-bromo-4-chloroacetophenone (275 g, 1.2 mole). Within 5 minutes a white precipitate had formed, and the mixture was stirred for 3.0 hours. The solid was collected by filtration and washed with chloroform (50 ml). The solid was then air-dried to give 386 g of crude adduct.

All of the addition product (386 g, 1.03 m) was combined with conc. HCl (1100 ml) and methanol (900 ml), and the solution was stirred for 0.5 hours when a precipitate formed. Stirring was continued for 22 hours and the solid was collected by filtration. The wet solid was stirred in 2-propanol for 2.0 hours. The solid was collected and air-dried to give the crude α-amino-4-chloroacetophenone-hydrochloride. This reaction was repeated on an equimolar scale beginning with the alkyl halide and hexamethylenetetramine, to give a combined weight of 488 g of crude α-amino-4-chloroacetophenone.hydrochloride. The crude solid was recrystallized from a solution of ethanol and concentrated hydrochloric acid (1%) to give 480 g (99%) of α-amino-4-chloroacetophenone.hydrochloride.

To a stirred mixture of the above acetophenone (155 g, 0.75 mole) and [[(2,4-dioxo-1-imidazolidinyl)imino]methyl]formyl chloride (143 g, 0.75 mole) was added a solution of dimethylformamide (775 ml) and pyridine (206 ml). The solution was stirred for 20 hours. The yellow solution was poured into water (15 l) and the precipitated solid was collected by filtration. The solid was air-dried to give 205 g (84%) of crude [2-(4-chlorophenyl)-2-oxoethyl]-[[(2,4-dioxo-1-imidazolidinyl)imino]methyl]formamide.

The above solid (150 g, 0.46 mole) was combined with phosphorus oxychloride (800 ml) and the mixture was stirred and refluxed for 1.25 hours. The cooled solution was stirred for 0.5 hour in a water and ice mixture (12 l) and the precipitated solid collected by filtration. Recrystallization from acetic acid gave 81.7 g (59%) in two crops of 1-[[[5-(4-chlorophenyl)-2-oxazolyl]methylene]amino]-2,4-imidazolidinedione, m.p. 290°–294° C. Overall yield was 44%.

Anal. Calcd. for $C_{13}H_9ClN_4O_3$: C, 51.24; H, 2.98; N, 1839; Found: C, 51.05; H, 3.11; N, 18.06.

EXAMPLE IX

1-[[[5-(3-Trifluoromethylphenyl)-2-oxazolyl)methylene]amino]-2,4-imidazolidinedione To a stirred cooled (0°–5°) solution of m-trifluoromethylacetophenone (50 g, 0.27 mole) anhydrous ether (270 ml) and dioxane (130 ml) was added bromine (15 ml, 0.27 mole) dropwise, keeping the temperature below 5° over a period of two hours. The solution was allowed to stand without further cooling overnight. The solution was washed with water (3 × 500 ml), and the organic layer was dried over magnesium sulfate and evaporated under reduced pressure to an oil.

The oil was added to a stirred mixture of hexamethylenetetramine (47 g, 0.30 mole) in carbon tetrachloride (600 ml). The mixture was stirred overnight, and a white solid precipitated from the mixture. The white addition product was collected by filtration and was allowed to air-dry to give 96 g.

A mixture of the above addition product, conc. hydrochloric acid (100 ml) and ethanol (800 ml) was stirred at room temperature for 24 hours. The mixture was filtered and the filter cake (ammonium chloride) was discarded. The filtrate was evaporated under reduced pressure to a residue. The residue was recrystallized from a solution of 1% conc. hydrochloric acid in isopropanol (800 ml) to give 37 g (two crops) of α-amino-m-trifluoromethylacetophenone. (The solution used was 1% conc. HCl:99% isopropanol).

A stirred mixture of N-[2-(3-trifluoromethylphenyl)-2-oxoethyl]-[[(2,4-dioxo-1-imidazolidinyl)methyl]-imino]formamide (39 g, 0.11 mole) and phosphorus oxychloride (300 ml) was refluxed for five hours. The mixture was stirred in ice water (6l) for one hour and the solid was collected by filtration. The solid was first recrystallized from nitromethane (800 ml, Darco) and then was recrystallized from acetic acid (75 ml) to give 15 g (16% yield overall).

A sample (0.7 g) was dried at 153° for 20 hours to give m.p. 239°–242°.

Anal Calcd. for $C_{14}H_9F_3N_4O_3$: C, 49.71; H, 2.68; N, 16.57; Found: C, 49.94; H, 2.64; N, 16.61.

What is claimed is:

1. A compound of the formula:

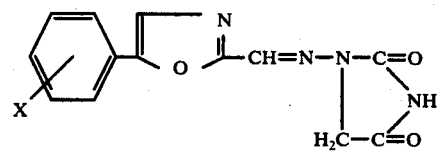

wherein X represents hydrogen, 4-halo, 3,4-dichloro, 4-nitro, 4-methoxy, 4-methyl or 3-trifluoromethyl.

2. The compound of claim 1 wherein X is 4-chloro.

3. The compound of claim 1 wherein X is 3,4-dichloro.

4. The compound of claim 1 wherein X is hydrogen.

5. The compound of claim 1 wherein X is 4-nitro.

6. The compound of claim 1 wherein X is 4-methoxy.

7. The compound of claim 1 wherein X is 4-bromo.

8. The compound of claim 1 wherein X is 4-fluoro.

9. The compound of claim 1 wherein X is 4-methyl.

10. The compound of claim 1 wherein X is 3-trifluoromethyl.

11. The method of preparing a compound of the formula:

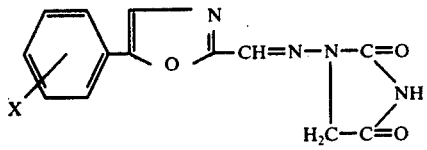

wherein X represents hydrogen, 4-halo, 3,4-dichloro, 4-nitro, 4-methoxy, 4-methyl or 3-trifluoromethyl which commprises causing cyclization in a compound of the formula:

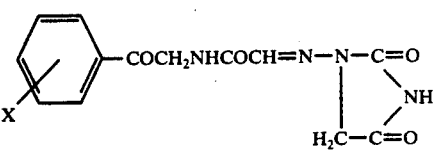

wherein X has the significance above given in the presence of phosphorus oxychloride.

* * * * *